(12) United States Patent
Meier

(10) Patent No.: US 7,516,740 B2
(45) Date of Patent: Apr. 14, 2009

(54) APPARATUS FOR SUPPLYING RESPIRATORY GAS AND A METHOD FOR CONTROLLING THE APPARATUS

(75) Inventor: Jörg Meier, München (DE)

(73) Assignee: MAP Medizin-Technologie GmbH, Martinsried (DE)

( * ) Notice: Subject to any disclaimer, the term of this patent is extended or adjusted under 35 U.S.C. 154(b) by 658 days.

(21) Appl. No.: 10/487,570

(22) PCT Filed: Aug. 15, 2002

(86) PCT No.: PCT/EP02/09147

§ 371 (c)(1),
(2), (4) Date: Feb. 20, 2004

(87) PCT Pub. No.: WO03/018096

PCT Pub. Date: Mar. 6, 2003

(65) Prior Publication Data

US 2004/0182386 A1    Sep. 23, 2004

(30) Foreign Application Priority Data

Aug. 20, 2001  (DE) ................. 101 39 881

(51) Int. Cl.
*A61M 15/00* (2006.01)
*A61M 16/00* (2006.01)
*A61M 16/10* (2006.01)
*F23D 11/00* (2006.01)
*F23D 14/00* (2006.01)

(52) U.S. Cl. .......... 128/203.16; 128/203.14; 128/203.26

(58) Field of Classification Search ......... 128/203.14, 128/203.16, 203.26
See application file for complete search history.

(56) References Cited

U.S. PATENT DOCUMENTS 5,558,084 A * 9/1996 Daniell et al. ......... 128/203.17

(Continued)

FOREIGN PATENT DOCUMENTS

DE         196 02 077 A1    8/1996

(Continued)

*Primary Examiner*—Justine R Yu
*Assistant Examiner*—Kristen C Matter
(74) *Attorney, Agent, or Firm*—Nixon & Vanderhye P.C.

(57) ABSTRACT

The invention concerns an apparatus for supplying a respiratory gas and a method of controlling the apparatus. In accordance with the invention there is provided an apparatus for supplying a respiratory gas comprising a conveyor device for conveying the respiratory gas, a conduit means for feeding the respiratory gas conveyed by the conveyor device to a person, and a humidification device for humidifying the respiratory gas, which is distinguished by a sensor device for generating a signal indicative in respect of the respiratory gas humidity and a control device for controlling the humidification device having regard to the signal which is generated by the sensor device and which is indicative in respect of the respiratory gas humidity. Furthermore there is proposed a method of supplying a respiratory gas to a patient, in which the respiratory gas is introduced by means of a conveyor device into a conduit system leading to a patient and is humidified, wherein the conveyor device is operated in such a way that a respiratory gas pressure which is above ambient pressure obtains in the air conduit system, which is distinguished in that signals indicative in respect of the relative and/or absolute humidity of the respiratory gas are generated by means of a sensor device and the humidity of the respiratory gas is adjusted on the basis of the signals generated in that way.

34 Claims, 2 Drawing Sheets

U.S. PATENT DOCUMENTS

| | | | |
|---|---|---|---|
| 5,769,071 A | | 6/1998 | Turnbull |
| 5,988,164 A | * | 11/1999 | Paluch .................. 128/203.26 |
| 6,349,724 B1 | * | 2/2002 | Burton et al. .......... 128/204.18 |
| 2001/0029340 A1 | | 10/2001 | Mault et al. |
| 2004/0074493 A1 | * | 4/2004 | Seakins et al. ......... 128/203.16 |
| 2004/0079370 A1 | * | 4/2004 | Gradon et al. ......... 128/203.26 |
| 2004/0102731 A1 | * | 5/2004 | Blackhurst et al. ............ 604/26 |

FOREIGN PATENT DOCUMENTS

| | | |
|---|---|---|
| DE | 199 28 003 A1 | 2/2000 |
| EP | 1 005 878 A2 | 7/2000 |
| GB | 2 338 420 A | 12/1999 |
| WO | WO 01/56454 A2 | 8/2001 |
| WO | PCT/EP02/09147 | 8/2002 |

\* cited by examiner

APPARATUS FOR SUPPLYING RESPIRATORY GAS AND A METHOD FOR CONTROLLING THE APPARATUS

This application is the U.S. national phase of International Application No. PCT/EP02/09147, filed Aug. 15, 2002 which designated the U.S. and claims priority to German Application No. 101 39 881.6, filed Aug. 20, 2001, the entire contents of each of which are hereby incorporated by reference.

FIELD OF THE INVENTION

The invention concerns an apparatus for supplying a respiratory gas and a method of controlling the apparatus.

BACKGROUND OF THE INVENTION

In particular for the treatment of sleep-related breathing disorders, it is possible to supply the patient with a respiratory gas, for example filtered ambient air, at a pressure which is increased in relation to the ambient pressure. A respiratory gas pressure which is in the range of between 4 and 18 mbar above the ambient pressure makes it possible to obviate obstructions in the region of the upper respiratory tracts.

It is possible for the pressure of the respiratory gas to be definedly varied. Thus it is possible in particular to control the pressure in such a way that lower respiratory gas pressures obtained during the expiration phases than during the inspiration phases. It is further possible to adapt the respiratory gas pressure in such a way that for example an increased respiratory gas is only set when the person to whom artificial respiration is to be given is in a predetermined stage in sleep. It is further possible for the respiratory gas supplied to the patient to be charged with selected additive substances and, in particular, humidified. Humidification of the respiratory gas can be effected by the gas being brought into contact with warmed water. The degree of humidification of the respiratory gas can be adjusted in that case by way of the temperature of the humidifying water.

SUMMARY OF THE INVENTION

The object of the invention is to provide an apparatus for and a method of supplying a respiratory gas to a breathing person, whereby improved physiological compatibility of the supply of respiratory gas is achieved.

According to the invention that object is attained by an apparatus having the features including a conveyor device for conveying the respiratory gas, a conduit means for feeding the respiratory gas conveyed by the conveyor device to a person, a humidification device for humidifying the respiratory gas, a sensor device for generating a signal indicative in respect of the respiratory gas humidity and a control device for controlling the humidification device having regard to the signal which is generated by the sensor device and which is indicative in respect of the respiratory gas humidity.

In that way it is advantageously possible to match the humidity state of the respiratory gas in a narrow tolerance range to the instantaneous physiological demands of the patient. In that way it is advantageously possible to ensure that the respiratory gas is not inadequately or excessively humidified by virtue of an adjustment which is initially implemented on the part of the patient in the context of a deep-sleep phase or upon a change in breathing characteristic.

In accordance with a particularly preferred embodiment of the invention the sensor device for generating a signal indicative in respect of the absolute and/or relative humidity of the respiratory gas is arranged in the region of a breathing mask provided for supplying the respiratory gas.

Alternatively thereto or in a particularly advantageous manner in combination with that feature it is also possible for a sensor device for producing a signal indicative in respect of the humidity state of the respiratory gas to be arranged at the outlet of an air humidification device. By virtue of combined consideration of an air humidity signal generated in the outlet region of an air humidification device and an air humidity signal generated in the region of the patient or mask, it is then possible to check whether an unacceptably great change in the humidity state of the respiratory gas and in particular precipitation of water takes place in the region of a respiratory gas conduit means provided between the breathing mask and the air humidification device.

It is also possible, for example by a temperature detection device provided in the region of the breathing mask, to detect the temperature of the respiratory gas in the region of the patient and, on the basis of an additional humidity signal produced for example in the region of an air humidification device, to assess whether an unacceptably high relative humidity level obtains in the respiratory gas in the region near the patient. Particularly in conjunction with a sensor device provided in the region of the patient for detecting a signal indicative in respect of the humidity state of the respiratory gas, it is advantageously possible to draw a distinction between expiratory humidity states and inspiratory humidity states.

The humidity states ascertained for the respective breathing phases can be taken into consideration in terms of regulating the respiratory gas humidity level, on the basis of a predetermined or preferably adaptively matched regulating procedure.

By virtue of the present invention it is possible to reduce the proportion of water which is entrained in drop form in the respiratory gas. That reliably avoids any germs being transported by way of drops of water.

In accordance with a particularly preferred embodiment of the invention the sensor device is arranged in the region, near a patient, of a respiratory gas conduit system. In that way it is advantageously possible to detect the respiratory gas humidity state which is actually relevant to the user. In that respect, in a particularly advantageous configuration, the sensor device is arranged in the region of a breathing mask and in particular is integrated into the breathing mask. In that respect the sensor device is preferably of such a design configuration that the measurement dynamics thereof are considerably higher than the breathing rate of the patient. In that way it is possible to specifically detect the humidity state of the respiratory gas for the respective breathing phases. The measurement values which are detected in that way for the expiration phase and for the inspiration phase, in regard to respiratory gas humidity level, can be evaluated by a preferably adaptively optimised regulating procedure. It is possible to disregard the respiratory gas humidity values ascertained in respect of the expiration phase or to take them into account only as control values, and to implement adjustment of the respiratory gas humidity essentially having regard to the respiratory gas humidity values detected in respect of the inspiration processes.

As an alternative to arranging the sensor device in the region near the patient—or in a particularly advantageous fashion in combination therewith—it is possible for the sensor device or a further sensor device to be arranged in the region between the breathing mask and a hose conduit portion, and in particular to integrate it into a coupling structure or a washing-out valve arrangement.

The sensor device can also be arranged in the region of the humidification device so that the humidity state of the respiratory gas can be directly detected by way of the sensor device and the operating performance of the humidification device can be matched in regard to a desired respiratory gas reference humidity state, having regard to the instantaneous respiratory gas humidity level.

In accordance with a particularly preferred embodiment of the invention the sensor device includes an electrical sensor element, wherein provided in the region of that sensor element is an electronic circuit, for the generation of a data sequence, by way of which the respiratory gas humidity measurement signals detected on the part of the sensor element can be transmitted in encoded form. Processing of the respiratory gas humidity signals detected by the sensor element in the region of the sensor element itself makes it possible substantially to avoid falsification of the signal, for example because of the transmission properties of any signal lines.

The sensor element is preferably designed in such a way that it detects the respiratory gas humidity on the basis of inductive, capacitive and/or thermal interaction effects. As an alternative thereto or also in combination with the use of physical measurement principles of that kind, it is also possible to detect the respiratory gas humidity by optical means.

In accordance with a particularly preferred embodiment of the invention a signal indicative in respect of the temperature of the respiratory gas is also generated on the part of the sensor device. Insofar as that is not the case, it is possible for a measuring device which is suitable for detecting the temperature of the respiratory gas to be preferably also arranged in the immediate proximity of the sensor element.

It is possible for the sensor device for detecting the respiratory gas humidity to be arranged in the region of the humidification device and for a temperature detection device to be provided in the region near the patient. On the basis of the respiratory gas humidity state detected in the region of the humidification device and the respiratory gas temperature detected in the region of the patient, it is possible to detect the relative humidity level of the respiratory gas at the patient. The measurement values detected on the part of the temperature detection device or also the humidity sensor device can also be taken into consideration in actuation of the conveyor device, besides actuation of the humidification device. Thus, on the basis of the measurement values generated by the humidity sensor device and/or the temperature detection device, it is possible to implement a breathing phase recognition operation and to modulate the respiratory gas pressure in accordance with the recognised breathing phases.

The operation of ascertaining a reference respiratory gas humidity value which is relevant for operation of the humidification device is preferably effected having regard to a data set, in particular an adaptively optimised data field, which takes account of the sleep state of the patient, the breath volume of the patient and for example also the position of sleep of the patient, and in particular the degree of neck rotation thereof. Thus it is possible for example, in periods of time in which the patient is sleeping on one side, to actuate lower respiratory gas humidity levels than for example in a situation involving a supply of respiratory gas when lying on the back.

Adjustment of the humidification output of the humidification device, such adjustment being effected in accordance with the signals generated by the humidity sensor device, is effected preferably by altering the temperature of the humidification water which comes into contact with the respiratory gas.

As an alternative to or also in combination with the above-described measure it is also possible to alter the humidification output of the humidification device for example by altering the effective water surface area available for humidification purposes. It is also possible for the respiratory gas temperature and in particular the temperature of the respiratory gas to be definedly adjusted before it comes into contact with the humidification water.

It is also possible to alter the flow characteristic of the air coming into contact with the humidification water, in such a way that the respectively desired respiratory gas humidity values checked by the sensor device occur at the outlet of the humidification device.

An embodiment of the invention, which is advantageous in regard to particularly precise conditioning of the respiratory gas in respect of the moisture contained therein is afforded if, if necessary, only a partial flow of the respiratory gas is brought into contact with the humidification water, wherein the respiratory gas humidity level is determined by way of the ratio of the partial flow of respiratory gas which has come into contact with the humidification water, and the partial flow of respiratory gas which is taken past the humidification device. It is possible for the conduit means to be passed through the humidification device in such a way that a respiratory gas which is pushed back over the humidification device during an expiration phase does not come into contact with the humidification water.

An embodiment of the invention, which is advantageous in regard to a particularly high level of handling comfort, is provided in that, disposed in the region of the sensor device for detecting the respiratory gas humidity is a transmitting device for wireless transmission of the data sequence generated in respect of the respiratory gas humidity. A transmitting device of that kind can be for example in the form of a blue tooth transmitting device. It is also possible for the signals generated on the part of the sensor device to be transmitted back to the humidification device optically, in particular in the form of infrared signals. When using a respiratory gas conduit produced from a material which is transparent at least in the infrared range, it is possible for the respiratory gas hose conduit to be used as an optical waveguide, by way of which the signals generated on the part of the sensor device can be transmitted to the humidification device or to a control device provided for controlling the humidification device.

The object of the invention as specified in the opening part of this specification is further attained in accordance with the invention by a method of supplying a respiratory gas to a patient, in which the respiratory gas is introduced by means of a conveyor device into a conduit system leading to a patient and is humidified, wherein the conveyor device is operated in such a way that a respiratory gas pressure which is above ambient pressure at least in phase-wise manner obtains in the air conduit system, wherein signals indicative in respect of the relative and/or absolute humidity of the respiratory gas are generated by means of a sensor device and the humidity of the respiratory gas is adjusted on the basis of the signals generated in that way.

In accordance with a particularly preferred embodiment of this method the humidity of the respiratory gas is detected in the region near the patient, in particular in the region of a breathing mask. In that way it is in particular possible to detect the respiratory gas humidity level both for the expiration phases and also for the inspiration phases and to take account of the measurement values individually obtained in that way, in ascertaining a reference respiratory gas humidity value.

The method according to the invention and also the above-described apparatus are particularly advantageously suitable for the artificial respiratory and breathing therapy sector. Humidification of the respiratory gas can also be effected in particular by ultrasonic atomisers, bubble vaporisers, surface contact humidifiers and injection systems. The dynamics of the respiratory gas humidification operation is preferably selected to be so high that in particular unacceptably high or also unacceptably low respiratory gas humidity values can be sufficiently quickly adjusted.

In regard to regulation of the respiratory gas temperature and/or the respiratory gas humidity content, preferably the following control parameters (X) are evaluated: the respiratory gas volume flow, the respiratory gas temperature, the humidity content of the respiratory gas in terms of relative and/or absolute humidity, levels of gas concentration, in particular $CO_2$ saturation, the therapy pressure and/or the mask pressure and/or the difference between a therapy reference pressure and the mask pressure actually occurring at the patient, polysomnographic parameters such as snoring, heart rate, oxygen saturation, body position; and ambient conditions such as air pressure, temperature and humidity and preferably also EEG-signals, in particular measurement values which are derived therefrom and are indicative in respect of the sleep phase.

The respiratory gas temperature and/or the respiratory gas humidity can be adjusted by way of the water surface area (preferably by varying the effective water surface area in the air humidifier) and/or the amount of water (preferably by means of the amount of water in the air humidifier) and/or the water temperature (preferably by heating or cooling the water and/or water molecules in the air) and/or the respiratory gas temperature (preferably by heating or cooling the respiratory air) and/or the mixing of gases (preferably by mixing various gases, for example dry air with mist of high humidity or also by mixing gas flows involving differing temperatures and/or air humidity levels and also by variable flow resistances in the region of the air humidifier.

BRIEF DESCRIPTION OF THE DRAWINGS

Further details of the invention will be apparent from the description hereinafter with reference to the drawing in which.

DETAILED DESCRIPTION

Figure 1:
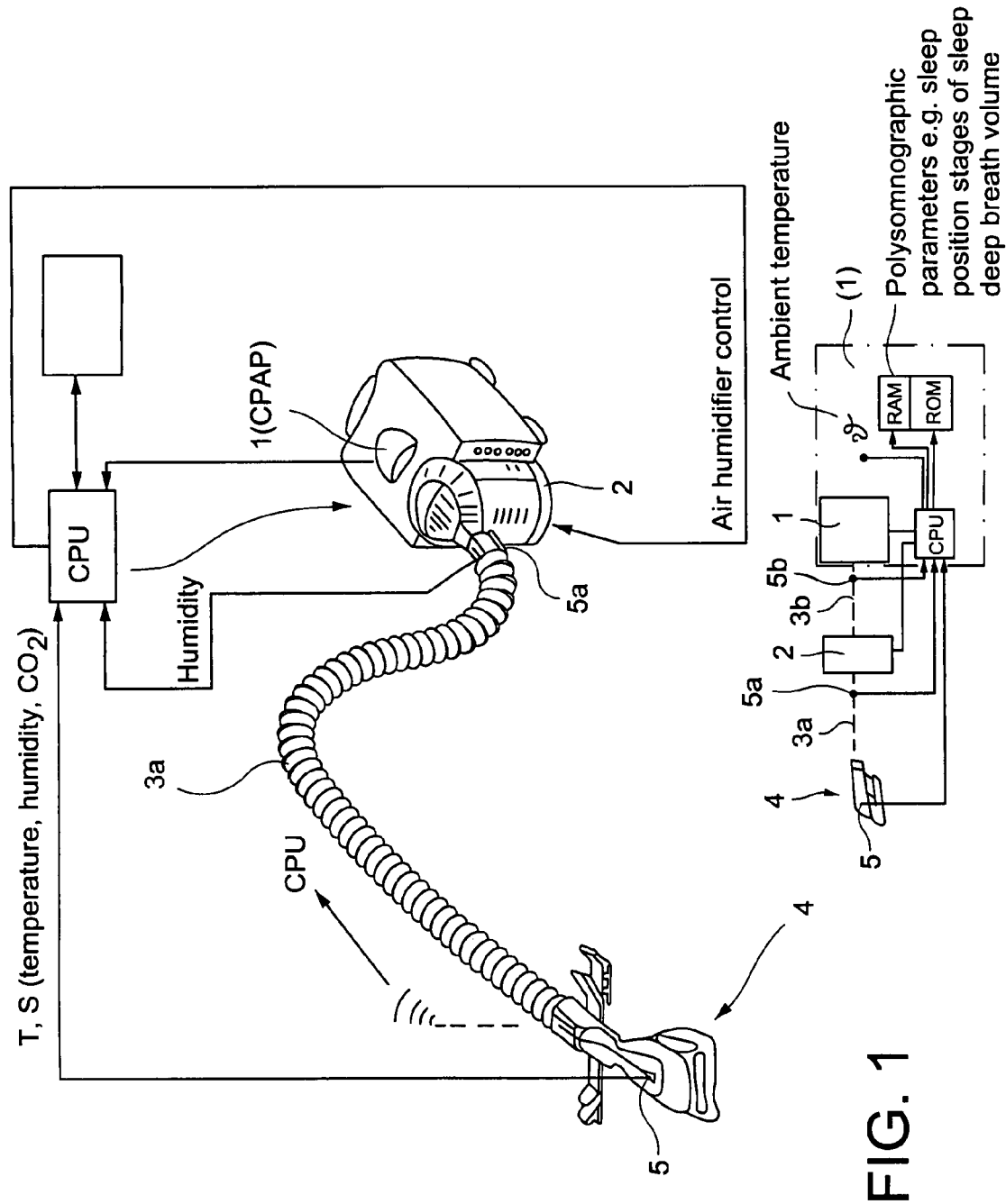
FIG. 1 is a simplified diagrammatic view to illustrate the structure of an apparatus according to the invention.

The system shown in FIG. 1 for supplying a respiratory gas includes a respiratory gas conveyor device 1, a respiratory gas humidification device 2 coupled thereto, and a breathing mask device 4 coupled to the respiratory gas humidification device 2 by way of a flexible hose conduit 3a.

The respiratory gas humidification device 2 can also be coupled in the form of what is known as a stand-alone unit to the respiratory gas conveyor device 1 by way of a preferably flexible hose conduit 3b. As an alternative thereto it is also possible for the respiratory gas humidification device 2 and the respiratory gas conveyor device 1 to be combined together to form an integral unit.

Disposed in the region of the conduit system which is provided to convey the respiratory gas and which is formed by the respiratory gas conveyor device 1, optionally the flexible hose conduit 3b, the respiratory gas humidification device 2, the flexible hose conduit 3a and in particular also the breathing mask device 4, there is at least one sensor device for detecting the humidity state of the respiratory gas being conveyed. In the embodiment illustrated here, provided in particular in the region of the breathing mask device 4 is a humidity sensor 5, by way of which a signal indicative in respect of the respiratory gas humidity state is generated and passed to a control device CPU. The control device CPU can either be arranged in the region of the humidity sensor 5 or can preferably be integrated into the respiratory gas humidification device or the respiratory gas conveyor device 1.

The respiratory gas humidification device 2 can be actuated on the basis of the signals generated on the part of the humidity sensor 5, in such a way that the humidity state of the respiratory gas which is humidified in the respiratory gas humidification device 2 takes account, in a close tolerance range, of the instantaneous physiological needs of the person being afforded respiration by way of the breathing mask device 4.

In determining the reference respiratory gas humidity state which is decisive at the present time, besides the signals generated by the humidity sensor 5, the procedure preferably also takes account of a performance graph or array which for example takes account of further polysomnographic parameters such as for example the degree of oxygen saturation of the blood of the person to whom respiration is being administered, noises, in particular snoring events as well as the heart rate and the instantaneous breathing characteristic. It is also possible, when calculating the reference humidity state of the respiratory gas, to take account of stages in sleep, ambient conditions as well as other physiological parameters, in particular the position in which the patient sleeps.

The system illustrated here has further sensor devices 5a, 5b by which signals are generated, used for defined conditioning of the respiratory gas. The sensor device 5b involves a sensor device for generating signals indicative in respect of the respiratory gas temperature: by taking account of the respiratory gas temperature signal generated on the part of the sensor device 5b, it is possible definedly to adapt the humidification output of the humidification device, as is required to achieve a desired reference humidity state.

It is possible by means of the sensor 5a provided in the region of the humidification device 2 to detect the humidity state of the respiratory gas immediately after it has been charged with water.

By taking account of the signal generated by the sensor device 5a disposed in the ambient region of the respiratory gas humidification device and also the signal generated by the sensor device 5 in the region near the mask, it is then possible to recognise any changes in state of the respiratory gas, caused by the flexible hose conduit 3a, in particular the formation of condensation water in the flexible hose conduit 3a, and on the basis thereof to implement corrections to the humidification output of the respiratory gas humidification device 2.

The sensor device 5 provided in the region of the breathing mask device 4 preferably includes a sensor element for detecting the humidity state on the basis of electromagnetic interactions, in particular capacitive interactions. The measurement signals generated by the sensor element are preferably converted into a digital data format by a connected measurement circuit while still in the region of the sensor element, and transmitted to the CPU by way of a preferably potential-free measurement data output.

It is possible for transmission of the humidity signals generated in the region of the breathing mask to be implemented by way of a data line which is preferably integrated into the flexible hose conduit 3a or is at least guided along same.

As an alternative thereto it is also possible for the measurement signals generated on the part of the humidity sensor 5 to be transmitted wirelessly, for example by way of a blue tooth arrangement, to the CPU or also to other detection devices. In this case the voltage supply for the humidity sensor 5 is preferably effected by means of a voltage source provided in the region of the breathing mask device 4, for example in the form of a button cell or a solar cell.

The respiratory gas humidification device 2 may include for example an ultrasonic atomising device, a bubble vaporiser or a surface contact humidifier. Preferably the humidification output of the humidification device 2 can be matched to the required humidification output within a time window which does not exceed a duration of 10 minutes.

Figure 2:
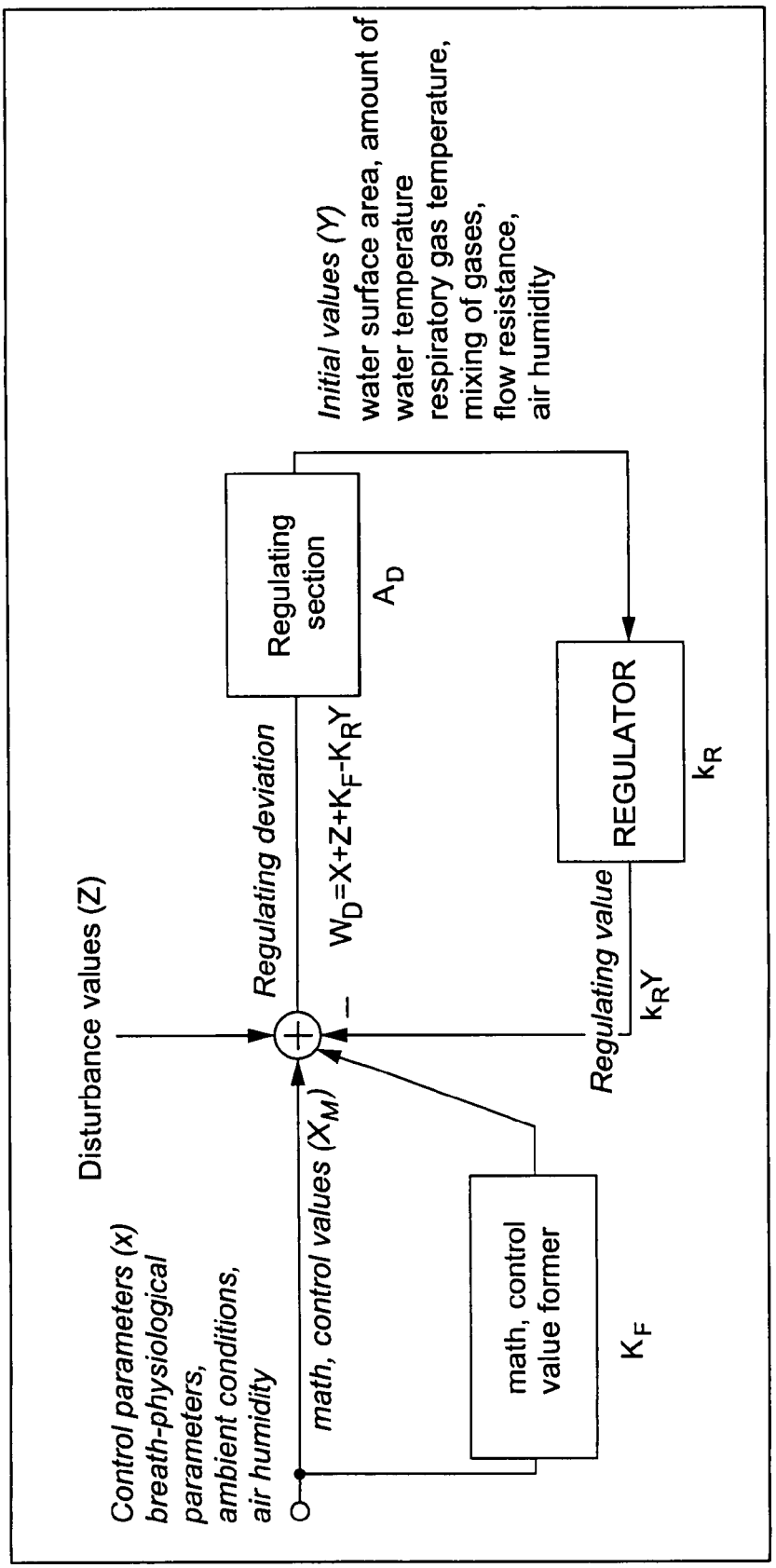
FIG. 2 shows a regulating circuit according to the invention for adjusting the respiratory gas humidity level.

FIG. 2 diagrammatically shows a preferred embodiment of a regulating circuit for controlling the humidity state of the respiratory gas. That regulating circuit makes it possible to individually match the respiratory gas temperature and/or the respiratory gas air humidity to the instantaneous physiological state of the patient, that is to say to increase it or reduce it in phase-wise manner.

Preferably the following control parameters (X) are evaluated for the purposes of regulating the respiratory gas state:
volume flow
respiratory gas temperature
humidity content of the respiratory air in terms of relative and/or absolute humidity
levels of gas concentration (gas composition, in particular $O_2$ content)
therapy pressure and/or mask pressure and/or delta between therapy pressure and the actually applied mask pressure
polysomnographic parameters such as snoring, heart rate, oxygen saturation, body position
ambient conditions such as air pressure, temperature and humidity content
EEG (sleep phase such as NREM 1-4, REM)
mathematical control values ($X_M$)
mathematical calculations from the control parameters.

Preferably the following initial parameters (Y) are regulated for the respiratory gas temperature and/or respiratory gas humidity:
water surface area (preferably by altering the effective water surface area in the air humidifier) and/or
amount of water (preferably by way of the amount of water which is in the air humidifier) and/or
water temperature (preferably by heating or cooling the water and/or water molecules in the air) and/or
respiratory gas temperature (preferably by heating or cooling the respiratory air) and/or
mixing gases (preferably by mixing various gases, for example dry air with mist/of high humidity at differing temperatures and/or with differing air humidity) and/or
flow resistances (preferably by way of the flow speed in the system).

The evaluation operation is preferably effected on the basis of the evaluation algorithm described hereinafter:

1st Feature

At least one control parameter (X) or a suitable combination is required for regulating the respiratory temperature and/or the respiratory humidity.

2nd Feature

The control parameters are evaluated over a given time interval, preferably over the expiration and inspiration time. The measurement values obtained in that way, within an interval, are subjected to further mathematical calculation, preferably maxima and/or minima and/or delta between minimum and maximum and/or mean values.

3rd Feature

Typical behaviour patterns on the part of the patients can be calculated from the control parameters (X). Thus, it is possible to establish the instantaneous breathing state by virtue of the reverse correlation of given control parameters (X), for example volume flow, temperature fluctuation in the respiration air, that is to say it is possible to draw a distinction between stable respiration (uniform amplitudes and regular respiration rate) and unstable respiration (irregular amplitude and respiration rate, periodic respiration) and regulation can be implemented on the basis of the mathematical control values ($X_M$).

The mode of operation of a respiratory gas supply system according to the invention is described hereinafter.

Control Parameters:

Volume Flow:

1. If the measured volume flow exceeds a limit value (for example due to mouth leakage), an increase in the respiratory gas temperature or an increase in respiration humidity is preferably effected. If the measured volume flow falls below a limit value (for example due to a low breath volume), cooling of the respiratory gas temperature or a reduction in respiration humidity is preferably effected.

2. A distinction can be made between stable respiration (uniform amplitude and regular respiration rate) and unstable respiration (irregular amplitude and respiration rate, periodic respiration) preferably by reverse correlation from the volume flow. The respiratory gas temperature and the respiration humidity is regulated by the result of the reverse correlation.

Respiratory Gas Temperature:

1. If the measured respiratory gas temperature falls below a limit value (for example due to mouth leakage), an increase in the respiratory gas temperature or an increase in respiratory gas humidity is preferably effected. If the measured respiratory gas temperature exceeds a limit value (for example due to a low breath volume), cooling of the respiratory gas temperature or a reduction in respiration humidity is preferably effected.

2. Both the temperature fluctuations during inspiration and expiration can be evaluated. The temperature difference measured from breathing in and breathing out is used as a regulating parameter. In the case of big breaths (large volume flow) the temperature delta between inspiration and expiration is highly pronounced so that preferably the respiratory gas temperature or respiration humidity is increased.

3. A distinction can be made between stable respiration (uniform amplitude and regular respiration rate) and unstable respiration (irregular amplitude and respiration rate, periodic respiration) preferably by reverse correlation from the respiratory gas temperature. The respiratory gas temperature and the respiration gas humidity is regulated by the result of the reverse correlation.

Humidity:

The respiratory air humidity is measured during expiration and inspiration. Humidity measurement can be effected both relatively and also absolutely.

1. The expiration and inspiration measurement values obtained in that way are further mathematically calculated, preferably over a time interval in which the minimum and/or the maximum and/or the delta between minimum and maximum and/or the mean value is formed.

2. The control parameter humidity can also be combined for example in dependence with the ambient temperature, kind of respiration (reverse correlation).

Initial Parameters:

Gas Concentration:

1. The respiratory gas humidity and/or the respiratory gas temperature can be regulated by mixing dry and humid air. Thus it is possible to branch off the air flow so that the air is passed over the surface of the water and/or over the cooling/heating means.

Flow Resistance:

1. The flow resistance within the air humidifier can be altered. If for example a high level of air humidity is required then contact or the residence time in the humidifier can be increased by increasing the flow resistance in the air humidifier.

The invention claimed is:

1. Apparatus for supplying a respiratory gas to a person comprising:
   - a conveyor device to convey the respiratory gas;
   - a breathing mask, worn by the person in use;
   - a hose conduit, arranged between the conveyor and the breathing mask, to feed the respiratory gas conveyed by the conveyor device to the person via the breathing mask;
   - a humidification device to humidify the respiratory gas;
   - a first sensor device, arranged on the breathing mask, to generate a signal indicative of the respiratory gas humidity;
   - a second sensor device arranged in the region of the humidification device at an outlet of the humidification device and configured to generate a signal indicative of the respiratory gas humidity;
   - a temperature detection device to detect a respiratory gas temperature change resulting from respiratory gas leakage near the breathing mask; and
   - a control device to control the humidification device, wherein the control device compares the signal from the first sensor device and the signal from the second sensor device to determine a change in the humidity of respiratory gas between the humidification device and the breathing mask, and wherein the control device is further adjusts the humidity and/or temperature of the respiratory gas when the detected respiratory gas temperature change resulting from respiratory gas leakage is below a certain threshold.

2. An apparatus according to claim 1, wherein the first sensor device includes an electronic sensor element, and wherein an electronic circuit is provided in the region of the first sensor element, the electronic circuit configured to generate a data sequence representative of the respiratory gas humidity detected by the first sensor element.

3. An apparatus according to claim 1, wherein the temperature detection device is arranged in the region of a breathing mask.

4. An apparatus according to claim 1, wherein the control device is arranged to adjust the humidity of the respiratory gas by adjusting the temperature of humidification water that comes into contact with the respiratory gas in the humidification device.

5. An apparatus according to claim 1, wherein the control device is arranged to adjust the humidity of the respiratory gas by varying effective contact surface available for humidification or the intensity of contact of the respiratory gas with a water surface.

6. An apparatus according to claim 1, wherein the control device is arranged to establish an amount of water introduced into the respiratory gas by the respiratory gas being brought into contact with a quantitatively controlled amount of water.

7. An apparatus according to claim 1, wherein the loading of the respiratory gas with water is adapted by controlling the respiratory gas temperature.

8. An apparatus according to claim 1, wherein the control device is arranged to adjust a degree of humidification of the respiratory gas by defined adjustment of a ratio of a partial flow of the respiratory gas which comes into contact with the humidification water and a partial flow of the respiratory gas that does not come into contact with the humidification water.

9. An apparatus according claim 1, wherein the control device is arranged to adjust a degree of humidification of the respiratory gas by adjustment of the respiratory gas flow coming into contact with humidification water.

10. An apparatus according to claim 1, further comprising a transmitting device to wirelessly transmit a data sequence indicative of the respiratory gas humidity arranged in the region of the first and/or second sensor device.

11. An apparatus according to claim 10, wherein the transmitting device is in the form of a blue tooth transmitting device.

12. The apparatus of claim 1, wherein the first sensor is at least configured to generate a signal indicative of the respiratory gas relative humidity and the second sensor is at least configured to generate a signal indicative of the respiratory gas relative humidity.

13. The apparatus of claim 1, wherein the first sensor is at least configured to generate a signal indicative of the respiratory gas absolute humidity and the second sensor is at least configured to generate a signal indicative of the respiratory gas absolute humidity.

14. The apparatus of claim 1, wherein the conveyor device is a positive airway pressure device.

15. An apparatus as in claim 1, wherein the second sensor device is operable to generate a signal indicative of at least one ambient condition.

16. A method of supplying a humidified respiratory gas above ambient pressure to a patient, in which a conveyor, including a humidification device, introduces the respiratory gas into a conduit system leading to a breathing mask in communication with an airway of the patient, the method comprising:
   - arranging a first sensor on the breathing mask;
   - arranging a second sensor on an outlet of the humidification device;
   - generating a first signal, indicative of relative and/or absolute humidity of the respiratory gas, using the first sensor;
   - generating a second signal, indicative of relative and/or absolute humidity of the respiratory gas using the second sensor;
   - comparing the first and second signals;
   - detecting a respiratory gas temperature change resulting from respiratory gas leakage near the breathing mask; and
   - adjusting the humidity of the respiratory gas on the basis of the comparison of the generated signals and the detected respiratory gas temperature change resulting from respiratory gas leakage.

17. A method according to claim 16 further including adjusting the temperature of the respiratory gas and/or the temperature of the humidification water to adjust the respiratory gas humidity level.

18. A method as in claim 16, further comprising:
generating a signal indicative of at least one ambient condition using the second sensor device.

19. Apparatus for supplying a respiratory gas to a person comprising:
a conveyor device to convey the respiratory gas;
a hose conduit, arranged between the conveyor and the person, to feed the respiratory gas conveyed by the conveyor device to the person;
a humidification device to humidify the respiratory gas;
a first sensor device configured to generate a signal indicative of one or more respiratory gas conditions, including respiratory gas humidity;
a second sensor device configured to generate a signal indicative of one or more ambient conditions, including ambient air humidity;
wherein the apparatus is further operable to detect a respiratory gas temperature change resulting from respiratory gas leakage near the breathing mask; and
a control device to control the humidification device, wherein the control device compares the signal from the first sensor device and the signal from the second sensor device to determine a change in the humidity of respiratory gas, and wherein the control device adjusts the humidity and/or temperature of the respiratory gas when the detected respiratory gas temperature change resulting from respiratory gas leakage is below a certain threshold.

20. The apparatus of claim 19, wherein the first sensor device is configured to generate a signal indicative of respiratory gas temperature and the second sensor device is configured to generate a signal indicative of ambient air temperature.

21. The apparatus of claim 20, wherein the control device is further configured to recognize, on the basis of the comparison of signals from the first and second sensor devices, the formation of condensation water in the hose conduit and, based on the recognition of the formation of condensation, implement corrections to a humidification output of the humidification device.

22. The apparatus of claim 19, wherein said second sensor device is further configured to generate a signal indicative of ambient air pressure.

23. The apparatus of claim 19, further including a breathing mask, worn by the person in use; wherein the first sensor device is arranged in the region of the breathing mask and the hose conduit connects to the breathing mask.

24. The apparatus of claim 23, wherein the control device is further configured to determine a change in the state of respiratory gas between the outlet of the humidification device and the first sensor device.

25. The apparatus of claim 23, wherein the first sensor device is integrated into the breathing mask.

26. The apparatus of claim 23, wherein the first sensor device is arranged in the region of a coupling structure provided between the breathing mask and the hose conduit.

27. The apparatus of claim 19, wherein the conveyor device is a positive airway pressure device.

28. An apparatus as in claim 19, wherein the control device is arranged to regulate a degree of humidification achieved by the action of the humidification device by adjusting the temperature of humidification water that comes into contact with the respiratory gas in the humidification device.

29. An apparatus as in claim 19, wherein the control device is arranged to regulate the humidification action of the humidification device by varying effective contact surface available for humidification or the intensity of contact of the respiratory gas with a water surface.

30. An apparatus as in claim 19, wherein the control device is arranged to establish an amount of water introduced into the respiratory gas by the respiratory gas being brought into contact with a quantitatively controlled amount of water.

31. An apparatus as in claim 19, wherein the loading of the respiratory gas with water is adapted by controlling the respiratory gas temperature.

32. An apparatus as in claim 19, wherein the control device is arranged to adjust a degree of humidification of the respiratory gas by defined adjustment of a flow characteristic of the respiratory gas which comes into contact with the humidification water.

33. An apparatus as in claim 19, wherein the control device is arranged to adjust a degree of humidification of the respiratory gas by adjustment of the respiratory gas flow coming into contact with humidification water.

34. An apparatus as in claim 19, further comprising a transmitting device to wirelessly transmit a data sequence indicative of a respiratory gas state arranged in the region of the first and/or second sensor device.

* * * * *